United States Patent [19]
VanBeneden

[11] Patent Number: 4,941,487
[45] Date of Patent: Jul. 17, 1990

[54] FLUORIDATED DENTAL FLOSS

[76] Inventor: Floyd V. VanBeneden, 26330 Shirley Ave., Euclid, Ohio 44132

[21] Appl. No.: 377,958

[22] Filed: Jul. 11, 1989

[51] Int. Cl.$^5$ ............................................. A61C 15/00
[52] U.S. Cl. ..................................... 132/323; 132/321; 132/324
[58] Field of Search ............... 132/321, 323, 324, 325, 132/326, 327

[56] References Cited

U.S. PATENT DOCUMENTS

| | | | |
|---|---|---|---|
| 2,748,781 | 6/1956 | Collat | 132/325 |
| 3,754,332 | 8/1973 | Warren, Jr. | 132/321 |
| 3,800,812 | 4/1974 | Jaffe | 132/321 |
| 3,897,795 | 8/1975 | Engel | 132/321 |
| 3,897,797 | 8/1975 | Erickson | 132/321 |
| 3,957,067 | 5/1976 | Ferraro et al. | 132/321 |
| 4,019,522 | 4/1977 | Elbreder | 132/322 |
| 4,414,990 | 11/1983 | Yost | 132/321 |
| 4,583,564 | 4/1986 | Finkelstein et al. | 132/321 |
| 4,638,823 | 1/1987 | Newman et al. | 132/321 |

Primary Examiner—John J. Wilson
Assistant Examiner—Frank A. LaViola, Jr.
Attorney, Agent, or Firm—Terry M. Gernstein

[57] ABSTRACT

Dental floss is covered with patches of fluoride so that a flossing procedure will expose a user's teeth to a source of flouride. The floss is either ribbon like or string like.

1 Claim, 1 Drawing Sheet

U.S. Patent  Jul. 17, 1990  4,941,487
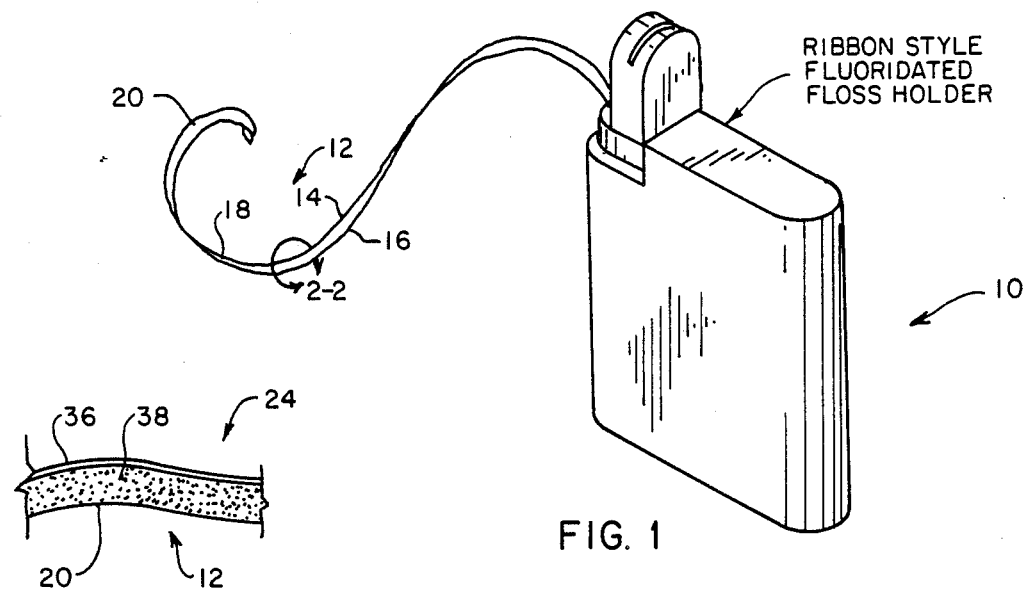
FIG. 1
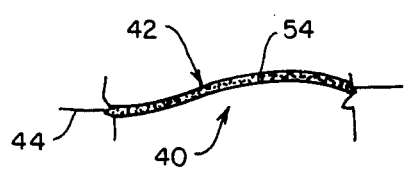
FIG. 2
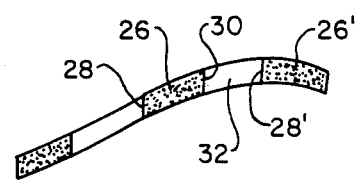
FIG. 3
FIG. 5
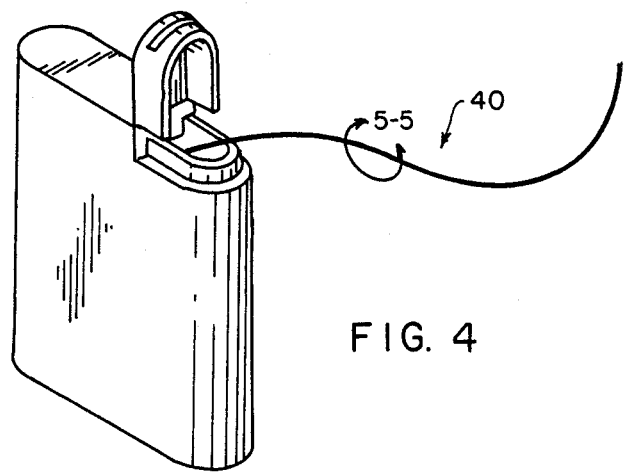
FIG. 4
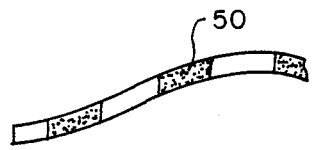
FIG. 6

FLUORIDATED DENTAL FLOSS

TECHNICAL FIELD OF THE INVENTION

The present invention relates to the general art of dentistry, and to the particular field of dental hygiene.

BACKGROUND OF THE INVENTION

The benefits of flossing one's teeth are well documented. Currently, dental health professionals suggest flossing at least once per day.

Due to the advantages of such flossing procedure, there are several proposals for various types of dental floss, such as ultra-thin floss, wax coated floss, and the like. See, for example the flosses disclosed in patents such as No. 3,771,536, 3,897,795 and 4,033,365.

While successful in accomplishing objectives of removing bacteria and the like from certain portions of the teeth, these known flosses still have a shortcoming associated with performing only a single operation, to wit: flossing.

If one is going to the trouble of flossing, it would appear to be efficient if more than a single procedure is carried out. The flossing devices known to the inventor only carry out the single function of flossing.

Still further, since floss is used by winding a substantial portion thereof about the user's fingers, any coating placed on the floss which is intended to further the flossing function is wasted on the floss wound on the user's fingers. For this reason, the known flosses are even less efficient.

Accordingly, there is a need for a dental floss which is more efficient in carrying out a plurality of operations and which is not wasteful of an coating material used on the floss.

More specifically, since the benefits of fluoride treatments for teeth are also well documented, it is known to add fluoride to drinking water and to toothpaste. However, such fluoride often does not reach the lateral edge surfaces of a user's teeth since such surfaces may abut each other so tightly as to prevent the fluoride from coating such surfaces.

Therefore, there is a further need for a means to coat the lateral edge surfaces of a person's teeth with fluoride to provide such surfaces with the benefits of a fluoride treatment.

OBJECTS OF THE INVENTION

It is a main object of the present invention to provide a dental floss which is more efficient in carrying out a plurality of operations and which is not wasteful of an coating material used on the floss.

It is another object of the present invention to provide a dental floss which is more efficient in carrying out a plurality of operations and which is not wasteful of an coating material used on the floss which will provide the benefits of a fluoride treatment to the lateral edges of a user's teeth.

It is another object of the present invention to provide a dental floss which is more efficient in carrying out a plurality of operations and which is not wasteful of an coating material used on the floss which will provide the benefits of a fluoride treatment to the lateral edges of a user's teeth in a manner that makes efficient use of the fluoride.

SUMMARY OF THE INVENTION

These, and other, objects of the present invention are achieved by coating a dental floss base material with patches of fluoride. The patches are spaced apart and are thin.

In this manner, a flossing process accomplishes a number of objectives. The flossing function is carried out, and at the same time, a fluoride treatment is performed on the edges of the teeth that are being flossed. Thus, the overall process is made more efficient than is presently available.

Further, since only patches of fluoride are used, the fluoride will be conserved as that portion of the floss that is wound about a user's fingers will not waste undue amounts of fluoride.

BRIEF DESCRIPTION OF THE DRAWING FIGURES

FIG. 1 is a perspective view of a container for a ribbon style fluoridated dental floss.

FIG. 2 is an enlarged view taken at section 2—2 of FIG. 11 showing a coating of fluoride on the ribbon style dental floss.

FIG. 3 is a view similar to FIG. 2 in which the patches of fluoride are indicated.

FIG. 4 is a perspective view of a thread-style fluoridated dental floss.

FIG. 5 is an enlarged view taken at section 4—4 of FIG. 4 showing a coating of fluoride on the thread-style dental floss.

FIG. 6 is a view similar to FIG. 5 in which the patches of fluoride are indicated.

DETAILED DESCRIPTION OF THE PREFERRED EMBODIMENT OF THE INVENTION

Shown in FIG. 1 is a dental floss container and dispenser 10. The container 10 is similar to the many dental floss containers and dispensers presently available and thus will not be discussed in detail.

Ribbon-like dental floss 12 is stored and dispensed from the container 10, and is elongated and of undefined length. The floss thus has a width as measured between edges 14 and 16, and a thickness as measured between top surface 18 and bottom surface 20. The ribbon floss is formed of material that is common to dental floss.

As best shown in FIG. 2, the floss 12 includes a layer 24 of fluoride. Such fluoride will thus be forced onto the edges of a user's teeth as he flosses.

As best shown in FIG. 3, the fluoride layer 24 is divided into a multiplicity of small patches, such as patch 26. The patches are spaced apart along the axis of the floss. The spacing between the patches is selected so that fluoride is not unduly wasted on that portion of the floss that is wound about a user's fingers, yet there is sufficient fluoride on the floss to ensure a complete fluoride treatment of the edges of the user's teeth during the flossing process as the floss is moved back and forth along the teeth. Specifically, a patch size of about one-half inch in length as measured between ends 28 and 30 of patch 26 and the size of space 32 between ends 30 and 28' of adjacent patches 26 and 26' of about one-half inch will achieve this goal. The thickness of the fluoride layer as measured between top surface 36 and bottom surface 38 thereof is less than about one mm, whereby the coated floss still will fit between a user's teeth even if such teeth are quite crowded.

Shown in FIGS. 4-6 is a thread-like fluoridated dental floss 40. The floss 40 is stored and dispensed from a container 10' and is elongated and of undefined length.

The floss 40 is coated as shown in FIG. 5 by having a sleeve-like coating 42 of fluoride surrounding the string-like base 44. The coating 42, also, is in patches, with a space between adjacent patches as indicated in FIG. 6. The patches, such as patch 50 are about one-half inch long and have a space therebetween of about one-half inch so that the above-discussed goal of efficient use of fluoride without significant waste can be achieved. The sleeves of fluoride are also less than about one mm in radius as measured from the string 44 to the outer surface 54 of the sleeve.

It is noted that the fluoride coatings on both forms of the floss can be applied using processes similar to those described in the aforementioned U.S. Pat. Nos. 3,771,536, 3,897,795 and 4,033,365, the disclosures of which are fully incorporated herein by reference. These processes will be modified to apply the fluoride in patches as above described.

It is understood that while certain forms of the present invention have been illustrated and described herein, it is not to be limited to the specific forms or arrangements of parts described and shown.

I claim:
1. Dental floss consisting entirely of:
   an elongated base of dental-floss material having an undefined length, said base being ribbon-like in form to have a rectangular cross-section;
   patches of fluoride on said base, said patches each being approximately one-half inch in length and being spaced apart about one-half inch, and being less than about one mm in thickness.

* * * * *